(12) United States Patent
Geus et al.

(10) Patent No.: US 6,195,413 B1
(45) Date of Patent: Feb. 27, 2001

(54) METHOD AND ARRANGEMENT FOR DETECTING X-RAYS

(75) Inventors: George Geus, Wiesbaden; Martin Hartick, Otzberg; Patricia Schall, Darmstadt, all of (DE)

(73) Assignee: Heimann Systems GmbH, Weisbaden (DE)

( * ) Notice: Subject to any disclaimer, the term of this patent is extended or adjusted under 35 U.S.C. 154(b) by 0 days.

(21) Appl. No.: 09/332,123

(22) Filed: Jun. 14, 1999

(30) Foreign Application Priority Data

Jun. 12, 1998 (DE) .............................. 198 26 062

(51) Int. Cl.[7] .............................. G01N 23/06; H05G 1/64
(52) U.S. Cl. .............................. 378/98.9; 378/57
(58) Field of Search ........................ 378/57, 98.9, 98.11, 378/98.12, 156

(56) References Cited

U.S. PATENT DOCUMENTS

| | | | |
|---|---|---|---|
| 4,029,963 | 6/1977 | Alvarez et al. | 378/5 |
| 4,626,688 | 12/1986 | Barnes | 250/361 R |
| 4,686,695 | 8/1987 | Macovski | 378/146 |
| 5,742,660 | * 4/1998 | Majewski et al. | 378/98.9 |
| 5,841,833 | * 11/1998 | Mazess et al. | 378/98.9 |

FOREIGN PATENT DOCUMENTS 0 398 029 A1    11/1990 (EP) .
1154973    6/1969 (GB) .

* cited by examiner

Primary Examiner—David P. Porta
Assistant Examiner—Drew A. Dunn
(74) Attorney, Agent, or Firm—Venable; Norman N. Kunitz

(57) ABSTRACT

A method for detecting X-rays which are separated into individual energy ranges after penetrating an object, as well as to an arrangement for implementing this method. It is known to detect X-rays (FX) by using detection devices (3), consisting of several identically configured detector pairs. The detector pairs in that case consist of a low-energy detector (4) and a high-energy detector (7). As a result, the weakened X-ray beam (FX') is separated into individual energy ranges following the X-raying of an object (2). This separation is necessary to determine the types of material in the X-rayed object (2). The disadvantage of known detection devices (3) is that an overlapping of the individual energy ranges occurs in the low-energy detector (4), thereby making it impossible to detect the material type with certainty. This problem is avoided by providing for computing out the high-energy shares absorbed in the low-energy detector (4) with the aid of an additional signal. For this purpose, a second low-energy detector (5) is arranged between the first low-energy detector (4) and the high-energy detector (7). An energy spectrum ($FX_2$) that is absorbed in the second low-energy detector (5) is used to obtain the signal to be subtracted.

10 Claims, 3 Drawing Sheets

METHOD AND ARRANGEMENT FOR DETECTING X-RAYS

CROSS-REFERENCE TO RELATED APPLICATIONS

The present application claims the right of foreign priority with respect to Application No. DE 19826062.8 filed in Germany on Jun. 12, 1998, the subject matter of which is incorporated herein by reference.

BACKGROUND OF THE INVENTION

The invention relates to a method for detecting X-rays where the individual energy ranges are simultaneously radiated onto an object to be X-rayed and are thereby weakened and, the weakened X-ray beams are separated into a low-energy range and a high-energy range. The invention additionally relates to an arrangement for implementing this method.

It is known to use a detection device, configured with several detector pairs, for the detection and determination of materials with the aid of X-rays. Each detector pair consists of one 0.1–0.5 mm thin and one 0.5–20 mm thick radiation detector. The radiation detectors are arranged one after another and are therefore penetrated successively by the X-rays or the roentgen quanta from a radiation source. The X-ray beam consequently is separated into individual energy ranges, which is necessary to determine the material types of a good examined with the aid of X-rays. The fact that photons with higher energy show little interaction in the thin detector, in the following called a low-detector, and are thus absorbed in the subsequent thick detector, in the following called a high detector, is used for the separation of the radiation into different energy ranges. In contrast, photons with low energy are absorbed almost completely in the low detector. The radiation impinging on the detector pairs changes as a result of the good or material to be tested, which is located between the radiation source and the detection device. Based on the change in the signals of each detector pair, it is then possible to draw conclusions as to the materials inserted into the ray path.

Since a certain interaction of the high-energetic photons in the low detector cannot be prevented, high-energy shares of the impinging radiation are also absorbed. As a result, an overlapping of the energy ranges occurs. Consequently, these traditional arrangements are not suitable for an exact material determination.

British patent reference GB-1154973 discloses a detector arrangement for taking an X-ray of a human body. In that case, a respective one filter is arranged between three X-ray films. Bones, muscles and fatty tissues are shown on the first X-ray film. The following first filter is dimensioned such that it filters out the energy shares of the bones so that only the energy shares of the muscles and the fatty tissue are shown on the second X-ray film. Subsequently, the energy shares for the fat or fatty tissue are filtered out in the second filter, so that only the energy shares for the muscles are captured on the third X-ray film. The X-ray picture is then composed of the image on the first X-ray film less the images from both the second and third X-ray films. For this, the first X-ray film is a film positive and the other two films are respectively film negatives. The resulting X-ray image represents the bone information.

U.S. Pat. No. 4,626,688 discloses a separated energy radiation detection with varied energy levels, which are generated and transmitted with a time displacement. Thus, a low frequency radiation is initially produced and is beamed through the body of a patient. A first detector absorbs this radiation and transmits the signals, resulting from the energy spectra, to a digital processor circuit. Subsequently, a higher frequency is generated and is beamed as radiation with higher energy through the patient and is then transmitted to the processor via a second detector. In the processor, the low frequency is subtracted from the high frequency, so that the low energy shares no longer form a component of the higher frequency. The higher frequency represents the bone information, as is known, so that the low energy shares of the soft body tissues are computed out of the high-energy shares through this measure. The image on a luminous screen again represents only the information on the X-rayed bones.

The disadvantage of the aforementioned arrangements and methods is that the energy ranges are reduced to an energy range that corresponds to the searched for material, so that the arrangements and methods can be used only if the materials and energy spectra to be detected are known ahead of time.

U.S. Pat. No. 4,029,963 discloses an arrangement and a method for detecting and identifying various materials. In this case, the transmitted X-rays are from the start separated into low-energy ranges and high-energy ranges, which are thus free of spectral displacements. A radiation depending on the atomic number Z, as well as a density-dependent radiation are determined from the separately transmitted rays through mathematical correlation. The radiation depending on the atomic number Z is proportional to the photoelectric component while the density-dependent radiation is proportional to the electrode density. The material is determined on the basis of this correlation.

It is the object of the invention to provide a method and an arrangement, which allow a clearer separation of low-energy shares and high-energy shares of a single X-ray beam. As a result, the X-rayed materials can be identified easier with only a single X-ray beam.

SUMMARY OF THE INVENTION

The above object generally is achieved according to one aspect of the present invention by a method for detecting X-rays where the individual energy ranges are simultaneously radiated onto an object to be X-rayed and are thereby weakened and, the weakened X-ray beams are separated into a low-energy range and a high-energy range, and wherein the high-energy shares absorbed in the low energy range are once more computed out of the low-energy range signal using an additional signal determined from another low-energy range signal that also represents the low-energy range of the weakened X-ray beam.

The above object generally is achieved according to a further aspect of the invention by an arrangement for implementing the above method with the arrangement comprising: an X-ray beam generator for directing an X-ray beam toward an object to be X-rayed: a detection device including several pairs of detectors with respectively one low detector and one high detector, and a subsequently installed computation unit and an image evaluation unit, and wherein each detector pair is provided with an additional low detector that provides the additional signal and is spatially integrated in the beam path between the first low detector and the high detector so that these detectors form a detector group.

The invention is based on the idea of creating the highest possible signal differences following penetration of an object, so that this will result in the best possible, meaning a high-contrast, separation of a X-ray beam into low-energy range and high-energy range. In addition to identifying the material, the method according to the invention is also used to determine the type of material, which occurs with the aid of the separated low-energy and high-energy ranges of this one X-ray beam. The polychromatic X-ray beam and thus all quanta up to the limit energy are radiated at the same time and are captured in the detectors at the same time, spatially one after another. For an improved separation, a signal is generated that corresponds to a high-energy share absorbed in a first detector. With this signal, the undesirable high-energy shares are computed out of the energy spectrum of the first detector. Several identical detector pairs, respectively consisting of a detector for low-energy shares and a detector for high-energy shares, are provided for this with an additional detector. This detector also absorbs the low-energy shares and is located between the low-detector and the high-detector, so that these detectors are successively penetrated by an X-ray beam that is weakened by the object. The second low detector is used to generate the signal with the undesirable high-energy share. For this, the second low detector has approximately the same absorption characteristic as the first low detector, particularly in the high-energy range.

Advantageous embodiments and modifications are described.

The high-energy shares absorbed in the first detector can be added to the high-energy shares of the high detector to create larger signal differences between low-energy shares and high-energy shares. This will also improve the high-energy share statistic.

The separation of the weakened X-ray beam occurs preferably for each pixel or picture element.

A high filter is advantageously inserted between the second low detector and the high detector. Moreover, the first low detector, the second low detector, as well as the high detector are connected to separate inputs of a computation unit, so that a low signal freed of high-energy shares is present at the output of the computation unit. In addition, an improved high signal is emitted at another output. Both outputs are connected to a subsequent image evaluation unit.

The second detector and the first detector each can be configured differently, wherein both detectors are optimally produced from the same material and have the same thickness.

The invention is explained in further detail below with the aid of an exemplary embodiment.

DETAILED DESCRIPTION OF THE PREFERRED EMBODIMENTS

Figure 1:
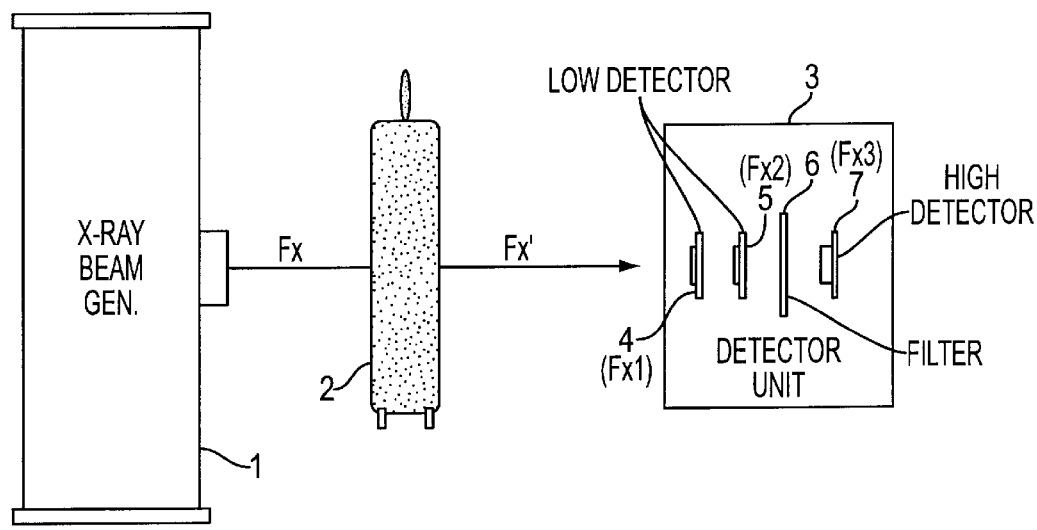
FIG. 1 shows an arrangement for detecting X-rays with the aid of 3 detectors.

FIG. 1 illustrates a simplified design of a X-ray arrangement, comprising a X-ray beam generator 1, an object 2 to be X-rayed, as well as a detection device 3. The complete detection device is generally line-shaped or planar and is composed of a plurality of detector groups 3 (here shown only once) having the same design. Each detector group 3 is composed of a first detector 4, a second detector 5, as well as a third detector 7, arranged in sequence one after another in the beam path. A filter 6 is preferably arranged between the second detector 5 and the third detector 7, which filter 6 serves to filter out low-energy shares that have remained in the spectrum. The first detector 4 and the second detector 5 are respectively low-energy detectors while the third detector 7 is a high-energy detector. The detector 4 and the detector 5 preferably show the same absorption behavior, wherein both detectors 4, 5 preferably have the same dimensions and are made of the same material. The low detectors 4, 5 in this case are thin, measuring 0.1–0.5 mm, while the high detector 7 has a thickness of 0.5–20 mm.

Figure 3:
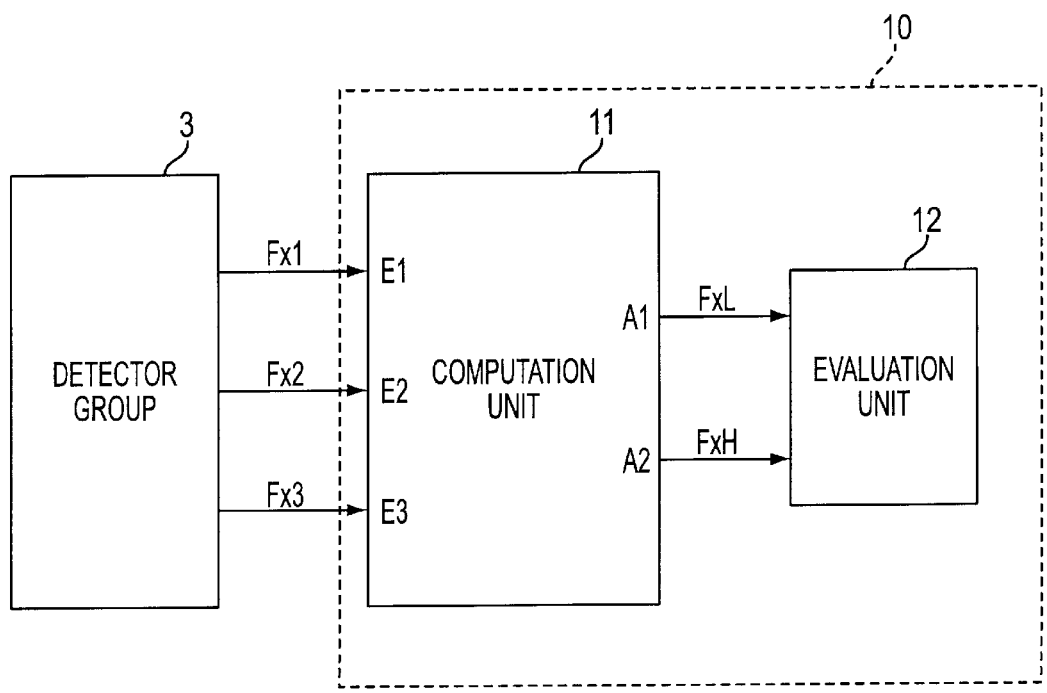
FIG. 3 shows a block diagram of an evaluation unit according to the invention.

FIG. 3 contains a block diagram of an evaluation unit 10, consisting essentially of a computation unit 11 and a subsequent image evaluation unit 12. An image display unit that is not shown in further detail here, e.g., a monitor screen, is connected in series after the image evaluation device 12.

Figure 2A:
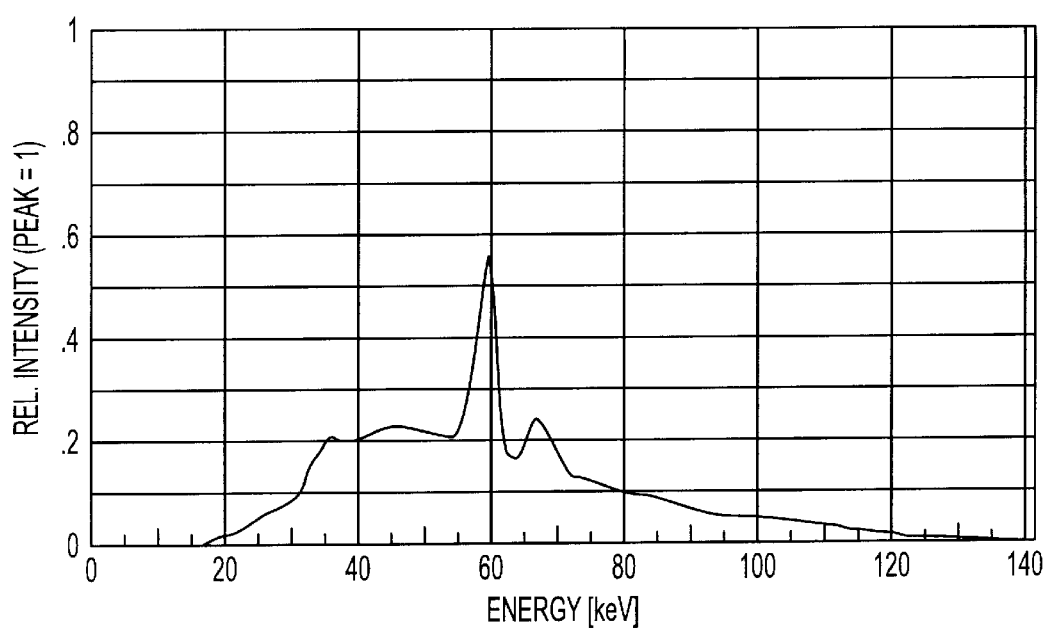
FIG. 2a shows an absorption curve for the first detector of FIG. 1.
Figure 2B:
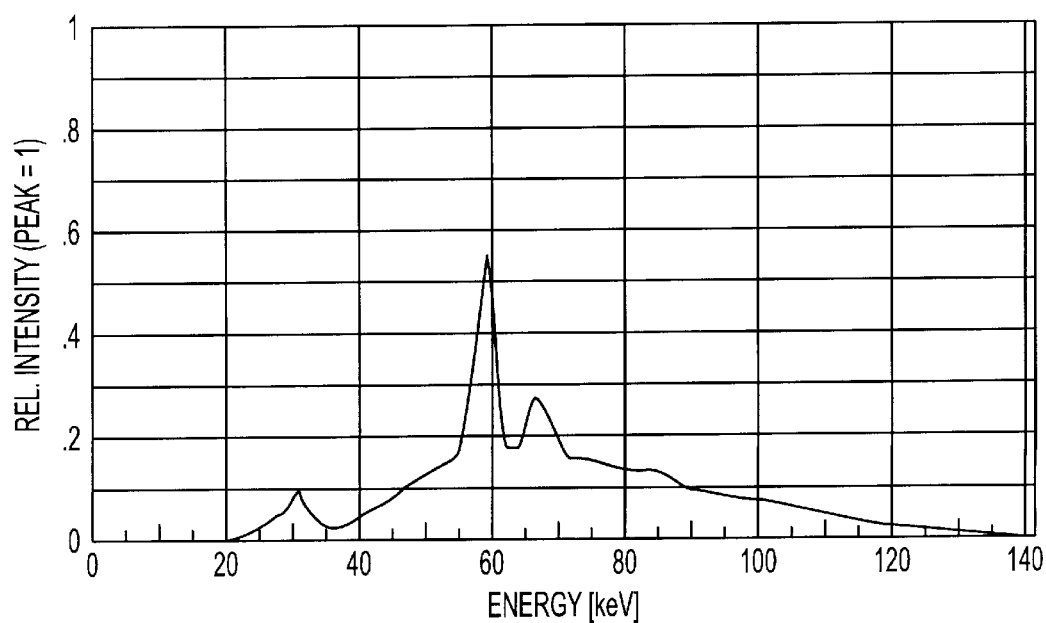
FIG. 2b shows an absorption curve for the second detector of FIG. 1.
Figure 2C:
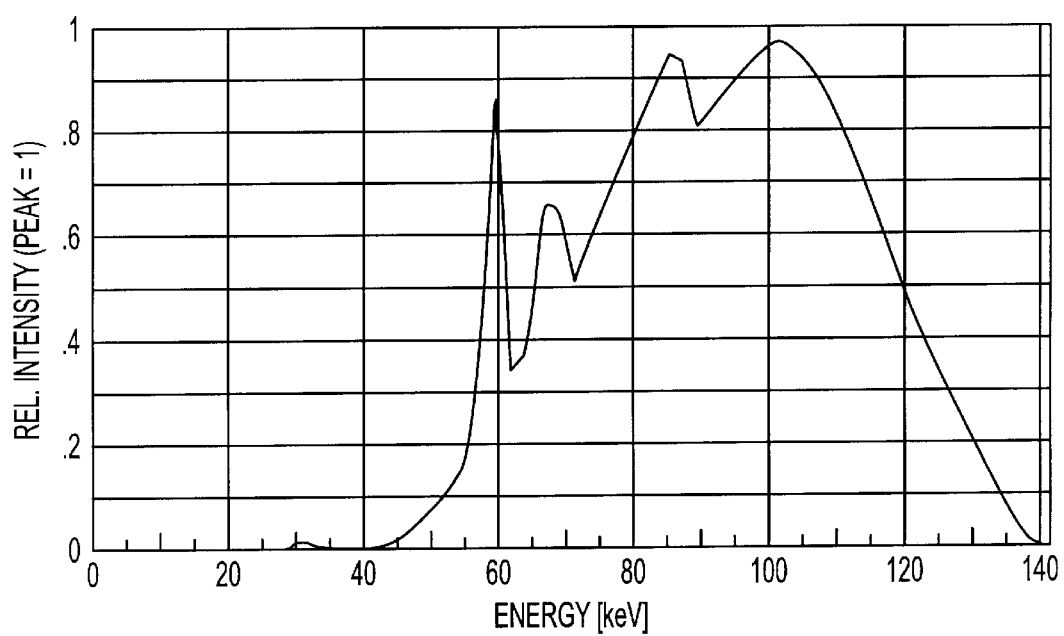
FIG. 2c shows an absorption curve for the third detector of FIG. 1.

The detection method involves the following processing steps:

The X-ray beam generator 1 generates an X-ray beam FX with an energy range of 10 to 500 keV, preferably 140 keV for this example. This X-ray beam FX penetrates the object 2 with the materials located therein (not shown here). Owing to the different absorption qualities of the materials in object 2, as well as the object 2 itself, a X-ray beam FX' with changed spectral composition and weakened intensity impinges on the detector group 3, and in particular the first detector 4. For each pixel, this detector 4 captures an energy spectrum $FX_1'$ that is shown in FIG. 2a and is changed by the object 2. In addition to the low-energy shares between 20 keV and 70 keV, this energy spectrum also contains high-energy shares between 70 keV to 140 keV. The reason for this is that it is not possible to prevent the previously mentioned interrelation of the high-energetic photons in the first detector 4. The amount and intensity of the absorbed high-energy shares in this case also depend on the X-rayed object 2. The absorbed energy spectrum $FX_1'$ travels as signal $FX_1$ to the input E1 of the computation unit 11. The second detector 5, which is connected in series after the first detector 4, catches the energy shares of the non-absorbed energy spectrum. As shown in FIG. 2b, this low detector 5 shows a similar absorption behavior as the detector 4 in the high-energy range between 30 keV and 70 keV, meaning the high-energy radiation shares are absorbed at the same ratio. A signal $FX_2$ of the energy spectrum $FX_2'$, obtained in this way from the detector 5, is conducted to another input E2 of the computation unit 11 to determine the high-energy share of detector 4. The high-energy shares of the X-ray beam FX', which were not captured or weakened by the detector 4 or the detector 5, travel to the high detector 7, wherein the remaining low-energy shares are filtered out of the energy spectrum by the filter 6. As shown in FIG. 2c, an energy spectrum $FX_3'$ is therefore present at the detector 7. This energy spectrum is also fed as signal $FX_3$ to an input E3 of the computation unit 11. The low-energy shares and the high-energy shares are then separated in the computation unit 11. The X-ray arrangement must first be calibrated so that the high-energy shares of the X-ray beam FX' can be computed out of the low signal $FX_1$. The correction values determined in this way, which take into account, for example, the offset behavior of the detectors 4 to 6, are stored in this computation unit 11. Following subtraction of the low signal $FX_2$ from the low signal $FX_1$ and thus of the high-energy share from the low signal $FX_1$, a new low signal $FX_L$ that is freed of high-energy shares is present at the output A1 of computation unit 11.

The high-energy share of the X-ray beam FX' is also determined in the computation unit 11, wherein the remaining low-energy shares are additionally filtered out of the energy spectrum $FX_2$' by inserting the filter 6 between the low detector 5 and the high detector 7.

In order to improve a statistic and thus reduce a noise, the high-energy shares absorbed in the detector 4, which were detected by the low detector 5, can be added to the high signal $FX_3$. Fo this, the low signal $FX_2$ is added to the high signal $FX_3$. A new high signal $FX_H$, which corresponds to the original high-energy range, is then present at output A1 of the computation unit 11.

The two separated signals $FX_L$ and $FX_H$ are transmitted to the image evaluation unit 12 where the materials in object 2 are evaluated and identified in the known way with the aid of different, stored characteristics.

As a result of this method according to the invention, the impinging X-ray spectrum or energy spectrum of the X-ray beam FX' is freed with the aid of two low detectors 4, 5 as well as the high filter 6 of low-energy shares in the spectrum. This information is improved as well by adding the signal, detected by the detector 5, to the high-energy share. A larger signal difference, with clear separation, is created between the low signal $FX_L$ and the high signal $FX_H$, thereby resulting in a more definite identification of the materials in object 2.

The material used for low detectors 4, 5 is cesium iodide, for example, and the material used for the high detector 7 is gadolinium oxysulfide.

It is understood that changes can be made within the framework of the inventive idea.

Thus, a preliminary filter (not shown here) can be installed on the X-ray beam generator 1 to further improve the separation qualities in the detector group 3. This preliminary filter is capable of changing the energy spectrum of the distributed rays FX that are emitted by the X-ray beam in such a way that the transition between the low-energy range and the high-energy range is weakened.

In addition, the detector group 3 can have more than two low detectors 4, 5 or additional intermediate filters (not shown here). Moreover, improved mathematical algorithms can be used in place of the subtraction according to the invention of the signals $FX_1$ from low detector 4 and the signals $FX_2$ from low detector 5.

The invention now being fully described, it will be apparent to one of ordinary skill in the art that many changes and modifications can be made thereto without departing from the spirit or scope of the invention as set forth herein.

What is claimed:

1. In a method for detecting X-rays where individual energy ranges are simultaneously radiated onto an object to be X-rayed and are thereby weakened and the weakened X-ray beams are separated into a low-energy range and a high-energy range by passing the weakened X-rays through sequentially arranged first low-energy range and high-energy range detectors to provide respective low-energy and high-energy signals, the improvement comprising: providing a further low-energy signal ($FX_2$) that also represents the low-energy range of the weakened X-ray beam (FX') from a second low energy detector; and using the further low-energy signal to compute the high-energy shares absorbed in the low energy range out of the low-energy signal ($FX_1$) provided by the first low-energy range detector to provide an improved low-energy range signal.

2. A method according to claim 1, further comprising adding the generated low energy signal ($FX_2$) from the second low energy detector, which generated signal represents the high-energy share in the low-energy signal, to a high signal ($FX_3$) that represents the high-energy range provided by the high-energy detector, in order to have an improved, clear separation between the low-energy range and the high-energy range of the weakened X-ray beam (FX').

3. A method according to claim 2, wherein the separation of the weakened X-ray beam (FX') into a low energy signal ($FX_L$) that is freed of high-energy shares and an improved high energy signal ($FX_H$) occurs for each pixel.

4. A method according to claim 1, wherein the material type of the object is identified by a comparison of the low energy signal ($FX_L$) and the high energy signal ($FX_H$), with stored signals that represent material data.

5. An arrangement for implementing the method according to claim 1, with said arrangement comprising: an X-ray beam generator for directing an X-ray beam onto an object to be X-rayed; a detection device including several pairs of detectors, with each pair including at least a first low energy range detector and one high energy detector arranged sequentially to detect the weakened X-ray beam to provide respective high-energy and low-energy signals; a subsequently installed computation unit for receiving the signals from the respective detectors and for providing improved low-energy and high-energy signals; and an image evaluation unit connected to outputs of the computation unit for receiving and evaluating output signals from the computation unit; and wherein each detector pair is provided with an second low detector that is spatially integrated between the first low energy detector and the high energy detector so that these detectors form a detector group.

6. An arrangement according to claim 5, wherein a filter is installed between the second low energy detector and the high energy detector.

7. An arrangement according to claim 5, wherein the first low energy detector is connected to a first input (E1) of the computation unit, the second low energy detector is connected to a second input (E2) of the computation unit, and the high energy detector is connected to another input (E3) of the computation unit.

8. An arrangement according to claim 7, wherein the computation unit subtracts the signals at said first and second inputs to provide a low energy signal ($FX_L$) that is freed of high-energy shares at a first output (A1) of the computation unit, and adds the signal at the second input of the computation unit to the signal at the third input of the computation unit to provide an improved high energy signal ($FX_H$) at a second output (A2) of the computation unit.

9. An arrangement according to claim 5, wherein the first low energy detector and the second low energy detector have the same absorption behavior.

10. An arrangement according to claim 5, wherein the first low energy detector and the second low energy detector are made from the same material and have the same dimensions.

* * * * *